United States Patent [19]

Hilboll et al.

[11] Patent Number: 4,643,998

[45] Date of Patent: Feb. 17, 1987

[54] IMIDAZOLYLALKYLTHIENYL TETRAHYDROPYRIDAZINES AND PROCESSES FOR THEIR USE

[75] Inventors: Gerd Hilboll, Cologne; Gerrit Prop, Pulheim; Harald Borbe, Cologne; Josef P. Löhr, Hilden; Ille-Stephanie Doppelfeld, Giessen, all of Fed. Rep. of Germany

[73] Assignee: A. Natterman & Cie GmbH, Cologne, Fed. Rep. of Germany

[21] Appl. No.: 545,623

[22] Filed: Oct. 26, 1983

[30] Foreign Application Priority Data

Nov. 6, 1982 [DE] Fed. Rep. of Germany ....... 3241102

[51] Int. Cl.$^4$ .................... C07D 237/06; A61K 31/50
[52] U.S. Cl. .................................. 514/252; 544/238; 544/239; 514/247
[58] Field of Search ................ 424/250; 544/238, 239; 514/252, 247

[56] References Cited

U.S. PATENT DOCUMENTS 4,353,905 10/1982 Sircar et al. ...................... 544/239
4,504,479 3/1985 Lautenschläger et al. ......... 514/252

Primary Examiner—Nicholas S. Rizzo
Attorney, Agent, or Firm—Pearne, Gordon, McCoy & Granger

[57] ABSTRACT

The invention relates to new imidazolylalkylthienyltetrahydropyridazines of the general formula I

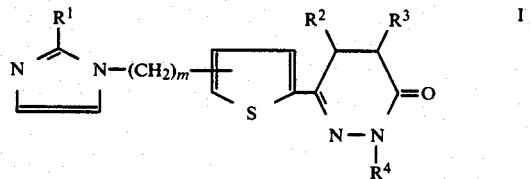

their acid addition salts as well as processes for their use in the treatment of cardiovascular and/or thromboembolic illnesses in humans.

7 Claims, No Drawings

IMIDAZOLYLALKYLTHIENYL TETRAHYDROPYRIDAZINES AND PROCESSES FOR THEIR USE

The present invention relates to new imidazolylalkylthienyl tetrahydropyridazines and their physiologically acceptable acid addition salts and to processes for their use as active ingredient in pharmaceuticals for the treatment of cardiovascular and/or thromboembolic illnesses in humans.

The imidazolylalkylthienyl tetrahydro pyridazines of the invention correspond to the general formula I

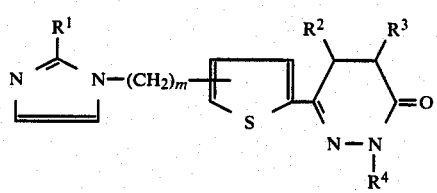

wherein $R^1$, $R^2$, $R^3$ and $R^4$ can be the same or different and independently of one another represent a hydrogen atom, a $C_{1-4}$ lower alkyl residue or a phenyl residue, while m stands for zero or a whole number from 1 to 8; but excluding compounds with a 2,5-disubstituted thiophene residue or thienyl radical, wherein $R^1$, $R^2$, $R^3$ and $R^4$ simultaneously represent hydrogen and m is other than zero.

Particularly preferred compounds are those with 2,5- or 2,4-disubstituted thiophene residues, in which m is zero and the pyridazine ring carries a methyl group in the 5-position.

Compounds according to the invention are, for example:

6-[5-(Imidazolylmethyl)-thien-2-yl]-3-oxo-2-phenyl-2,3,4,5-tetrahydro-pyridazine.
6-[4-(1-Imidazolylmethyl)-thien-2-yl]-3-oxo-2,3,4,5-tetrahydro-pyridazine.
6-[5-(1-Imidazolyl)-thien-2-yl]-5-methyl-3-oxo-2,3,4,5-tetrahydro-pyridazine.
6-[5-(1-Imidazolyl)-thien-2-yl]-2,5-dimethyl-3-oxo-2,3,4,5-tetrahydro-pyridazine.
6-[5-(2-Methyl-1-imidazolyl)-thien-2-yl]-5-methyl-3-oxo-2,3,4,5-tetrahydro-pyridazine.
6-[4-(1-Imidazolyl)-thien-2-yl]-5-methyl-3-oxo-2,3,4,5-tetrahydro-pyridazine.

The acid addition salts of compounds of the formula I are also included. Acid addition salts, for preference, are pharmaceutically acceptable or usable, e.g. those of hydrochloric acid, hydrobromic acid, sulfuric acid or phosphoric acid, or of organic acids, such as corresponding carboxylic acids e.g. acetic acid, propanoic acid, oxalic acid, malonic acid, glycolic acid, succinic acid, maleic acid, fumaric acid, malic acid, citric acid, tartaric acid.

The compounds of the formula I possess a centre of chirality at positions 4 and 5 of the pyridazine ring, if the substituents $R^2$ and/or $R^3$ are other than hydrogen; they can accordingly occur as racemic mixtures or in the form of the enantiomers. If separation of the racemic mixture is desired, this is usefully carried out by methods known per se with an optically active acid, e.g. dibenzoyl tartaric acid or camphor-10-sulfonic acid by formation of diastereomeric salts or by chromatography on optically active column material.

The compounds of the formula I according to the invention possess valuable pharmacological properties. In particular they are distinguished by pronounced hypotensive as well as anti-thrombotic activity. They also influence the metabolism of arachidonic acid and exhibit an antagonistic activity in relation to some physiological processes governed by PAF (Platelet Activating Factor). The compounds of formula I furthermore have a favourable influence on asthmatic complaints, and display anti-rheumatic and anti-atherosclerotic activity. They can therefore be used for the treatment of cardiovascular and thromboembolic illnesses, particularly in the human being.

If desired, the compounds of the formula I can be combined with diuretics and/or beta-blockers, preferably in usual dosages for such compounds.

Preparation of the substances of the formula I in accordance with the invention takes place by reaction of the 4-[(imidazolylalkyl)-thien-2-yl]-4-oxobutyric acids or their alkyl esters of the formula II, in which $R^1$, $R^2$, $R^3$ and m have the meaning given in formula I and $R^5$ denotes hydrogen or $C_{1-6}$ alkyl, with a hydrazine compound of the formula III, in which $R^4$ has the meaning given in formula I, the hydrate or salt thereof, such as the hydrochloride, the hydrogen sulfate, the sulfate etc, in aqueous, aqueous/alcoholic or alcoholic media or in solvents which are inert in the chosen conditions, e.g. dioxan, toluene, dimethylformamide or mixtures thereof with water or alcohol at temperatures of 30°–150° C., if necessary with the aid of a catalyst customary for aminolyses and condensation reactions, e.g. barium oxide, preferably at 80°–100° C. in ethanol or water.

The reaction is represented by the following scheme:

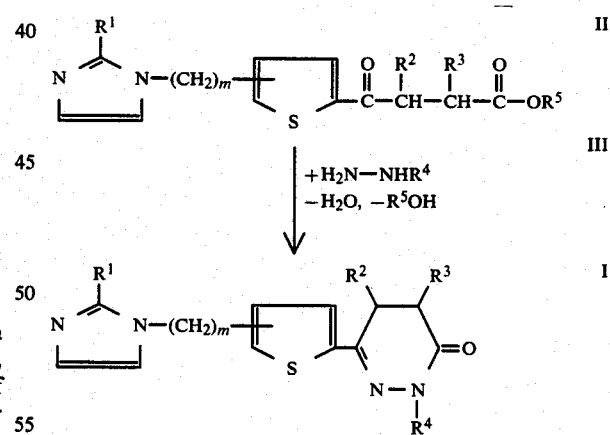

Starting substances of the formula II are especially the following:

4-[5-(1-Imidazolylmethyl)-thien-2-yl]-4-oxobutyric acid and its $C_{1-6}$-alkyl esters,
4-[5-(2-Methyl-1-imidazolylmethyl)-thien-2-yl]-4-oxobutyric acid and its $C_{1-6}$-alkyl esters,
4-[5-(2-Ethyl-1-imidazolylmethyl)-thien-2-yl]-4-oxobutyric acid and its $C_{1-6}$-alkyl esters,
4-[5-(2-Propyl-1-imidazolylmethyl)-thien-2-yl]-4-oxobutyric acid and its $C_{1-6}$-alkyl esters,
4-{5-[2-(2-Methyl-1-imidazolyl)-ethyl]-thien-2-yl}-4-oxobutyric acid and its $C_{1-6}$-alkyl esters, 4-{5-[3-(2-Methyl-1-imidazolyl)-propyl]-thien-2-yl}-4-oxo-butyric acid and its $C_{1-6}$-alkyl esters,
4-{5-[4-(2-Methyl-1-imidazolyl)-butyl]-thien-2-yl}-4-oxo-butyric acid and its $C_{1-6}$-alkyl esters,
4-{5-[5-(2-Methyl-1-imidazolyl)-pentyl]-thien-2-yl}-4-oxo-butyric acid and its $C_{1-6}$-alkyl esters,
4-{5-[6-(2-Methyl-1-imidazolyl)-hexyl]-thien-2-yl}-4-oxo-butyric acid and its $C_{1-6}$-alkyl esters,
4-{5-[7-(2-Methyl-1-imidazolyl)-heptyl]-thien-2-yl}-4-oxo-butyric acid and its $C_{1-6}$-alkyl esters,
4-{5-[8-(2-Methyl-1-imidazolyl)-octyl]-thien-2-yl}-4-oxo-butyric acid and its $C_{1-6}$-alkyl esters,
4-[4-(1-imidazolylmethyl)-thien-2-yl]-4-oxobutyric acid and its $C_{1-6}$-alkyl esters,
4-[4-(2-Methyl-1-imidazolylmethyl)-thien-2-yl]-4-oxobutyric acid and its $C_{1-6}$-alkyl esters,
4-[4-(2-Ethyl-1-imidazolylmethyl)-thien-2-yl]-4-oxobutyric acid and its $C_{1-6}$-alkyl esters,
4-[4-(2-Propyl-1-imidazolylmethyl)-thien-2-yl]-4-oxobutyric acid and its $C_{1-6}$-alkyl esters,
4-[5-(1-Imidazolyl)-thien-2-yl]-4-oxobutyric acid and its $C_{1-6}$-alkyl esters,
4-[5-(1-Imidazolyl)-thien-2-yl]-2-methyl-4-oxobutyric acid and its $C_{1-6}$-alkyl esters,
4-[5-(1-Imidazolyl)-thien-2-yl]-3-methyl-4-oxobutyric acid and its $C_{1-6}$-alkyl esters,
4-[5-(1-Imidazolyl)-thien-2-yl]-2-ethyl-4-oxobutyric acid and its $C_{1-6}$-alkyl esters,
4-[5-(1-Imidazolyl)-thien-2-yl]-3-ethyl-4-oxobutyric acid and its $C_{1-6}$-alkyl esters,
4-[5-(1-Imidazolyl)-thien-2-yl]-4-oxo-2-propyl-butyric acid and its $C_{1-6}$-alkyl esters,
4-[5-(1-Imidazolyl)-thien-2-yl]-4-oxo-3-propyl-butyric acid and its $C_{1-6}$-alkyl esters,
4-[5-(1-Imidazolyl)-thien-2-yl]-3-isopropyl-4-oxobutyric acid and its $C_{1-6}$-alkyl esters,
4-[5-(1-Imidazolyl)-thien-2-yl]-4-oxo-2-phenyl-butyric acid and its $C_{1-6}$-alkyl esters,
4-[5-(1-Imidazolyl)-thien-2-yl]-4-oxo-3-phenyl-butyric acid and its $C_{1-6}$-alkyl esters,
4-[5-(2-Methyl-1-imidazolyl)-thien-2-yl]-4-oxobutyric acid and its $C_{1-6}$-alkyl esters,
4-[5-(2-Methyl-1-imidazolyl)-thien-2-yl]-2-methyl-4-oxobutyric acid and its $C_{1-6}$-alkyl esters,
4-[5-(2-Methyl-1-imidazolyl)-thien-2-yl]-3-methyl-4-oxobutyric acid and its $C_{1-6}$-alkyl esters,
4-[5-(2-Ethyl-1-imidazolyl)-thien-2-yl]-4-oxobutyric acid and its $C_{1-6}$-alkyl esters,
4-[5-(2-Ethyl-1-imidazolyl)-thien-2-yl]-2-methyl-4-oxobutyric acid and its $C_{1-6}$-alkyl esters,
4-[5-(2-Ethyl-1-imidazolyl)-thien-2-yl]-3-methyl-4-oxobutyric acid and its $C_{1-6}$-alkyl esters,
4-[5-(2-Propyl-1-imidazolyl)-thien-2-yl]-4-oxobutyric acid and its $C_{1-6}$-alkyl esters,
4-[5-(2-Propyl-1-imidazolyl)-thien-2-yl]-3-methyl-4-oxobutyric acid and its $C_{1-6}$-alkyl esters,
4-[5-(2-Phenyl-1-imidazolyl)-thien-2-yl]-3-methyl-4-oxobutyric acid and its $C_{1-6}$-alkyl esters,
4-[4-(1-Imidazolyl)-thien-2-yl]-4-oxobutyric acid and its $C_{1-6}$-alkyl esters,
4-[4-(1-Imidazolyl)-thien-2-yl]-2-methyl-4-oxobutyric acid and its $C_{1-6}$-alkyl esters,
4-[4-(1-Imidazolyl)-thien-2-yl]-3-methyl-4-oxobutyric acid and its $C_{1-6}$-alkyl esters,
4-[4-(2-Methyl-1-imidazolyl)-thien-2-yl]-3-methyl-4-oxobutyric acid and its $C_{1-6}$-alkyl esters.

Starting compounds of the formula III are in particular the following:
hydrazine, methylhydrazine, ethylhydrazine, propylhydrazine, phenylhydrazine as well as their hydrates or salts, e.g. hydrochlorides, hydrogen sulfates, sulfates etc.

Preparation of the starting substances of the formula II takes place by procedures known per se:

(a) starting substances of the formula II with m other than zero:

1-(ω-Thienylalkyl)-imidazoles are prepared by alkylation of imidazoles with ω-halogenoalkyl thiophenes, if necessary 1-(ω-thienylalkyl)-imidazoles are prepared by alkylation of imidazoles with ω-halogenoalkyl thiophenes, if necessary with addition of an organic solvent, e.g. dimethylformamide, with optional use of an adjuvant base, e.g. sodium hydride (GB-PS No. 2031408).

The 1-(ω-thienylalkyl)-imidazoles are converted to the 4-[ω-(1-imidazolyl)-alkyl-thien-2-yl]-4-oxobutyric acid alkyl esters of the formula II by known processes with succinic acid alkyl ester chloride, with addition of an organic solvent e.g. 1,2-dichloroethane, nitrobenzene, carbon disulfide, using a Friedel-Crafts catalyst, e.g. aluminum chloride. The resulting esters of formula II are then hydrolysed by known methods to the corresponding 4-[ω-(1-imidazolyl)-alkylthien-2-yl]-4-oxobutyric acids.

The reactions take place according to the following scheme of formulas:

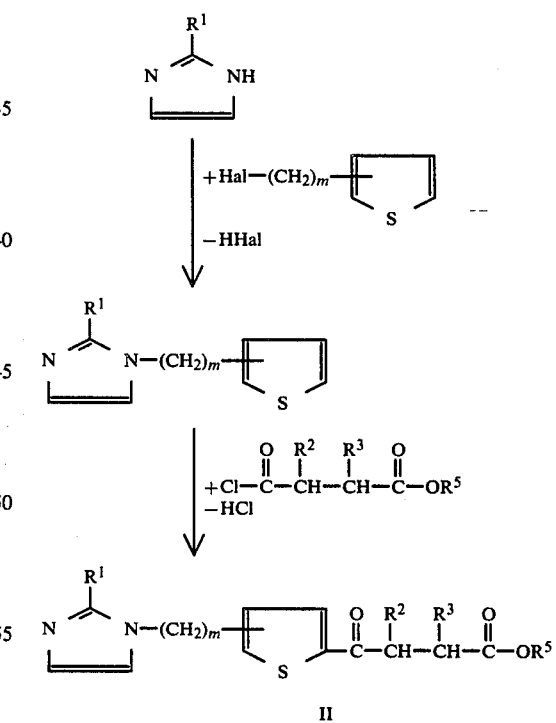

(b) starting substances of the formula II with m=0.
Bromothiophene-2-aldehydes are converted to the 1-imidazolyl-thiophene-2-aldehydes by means of imidazoles by heating with potassium carbonate in pyridine with copper oxide catalysts [J. B. Polya et al, J. Chem. Soc. C (1970), 85 to 91 ff] or by heating with potassium carbonate in nitrobenzene with copper bromide catalysis [L. M. Sitkina, A. M. Simonov, C.A. 65 (1966), 1368e]. The product aldehydes are converted to the corresponding 4-(1-imidazolyl-thien-2-yl)-4-oxobutyronitriles by means of 2-alkenoic acid nitriles under the catalytic influence of sodium cyanide [H. Stetter, Angew. Chem. Int. Ed. Engl. 15 (1976), 639 ff., or Organic Synthesis, vol. 59, p. 53 to 57]. The product nitriles are transformed by acid hydrolysis into the 4-(1-imidazolyl-thien-2-yl)-4-oxo-butyric acids of the formula II.

The conversions proceed according to the following reaction scheme:

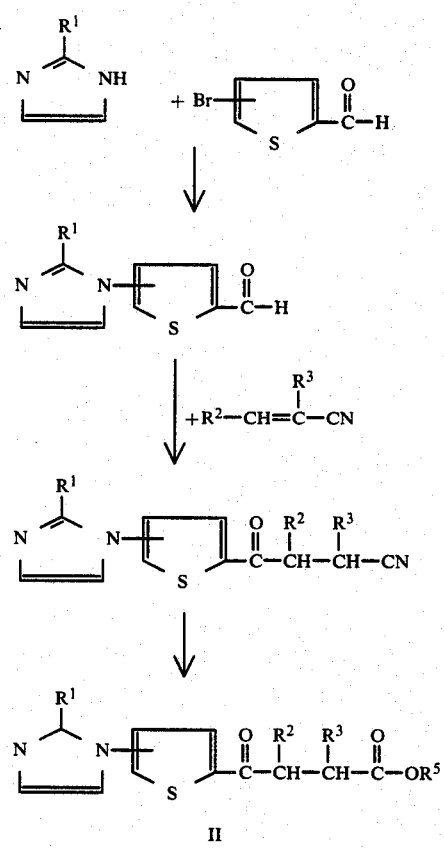

II

The acid addition salts of compounds of the formula I with inorganic or organic acids can be prepared by mixing the basic imidazolyl compounds with the corresponding acids in aqueous, aqueous/organic (e.g. alcohol-water) or organic media, e.g. alcohols, alcohol-ether mixtures or ether-petroleum ether mixtures at temperatures between 0° and 100° C.

The present invention relates likewise to pharmaceutical preparations which contain compounds of the formula I or pharmaceutically usable acid addition salts of these compounds. The pharmaceutical preparations according to the invention include some for enteral (e.g. oral or rectal) as well as parenteral administration, containing the pharmaceutical active ingredients alone or together with a conventional, pharmaceutically usable carrier material. The pharmaceutical preparation of the active ingredient is advantageously presented in the form of single doses, adapted to the desired form of administration, e.g. tablets, dragees, capsules, suppositories, granulates, solutions, emulsions or suspensions. The dosage of the compounds normally lies between 1.0 and 500 mg per dose, preferably between 5 and 150 mg per dose. The preparations can be administered once a day or several times a day such as three times, preferably two to three times a day.

The preparation of the compounds according to the invention is described in more detail by the following examples. The given melting points were measured with a Buechi 510 melting point determination apparatus and are given in °C., uncorrected. The IR spectra were read with a Perkin Elmer 257 or a Nicolet NIC-3600 device, and the mass spectra with the Varian MAT-311-A (70 eV) device.

EXAMPLE 1

6-[5-(2-Methyl-1-imidazolylmethyl)-thien-2-yl]-3-oxo-2,3,4,5-tetrahydro-pyridazine A mixture of 3 g of 4-[5-(2-methyl-1-imidazolylmethyl)-thien-2-yl]-4-oxobutyric acid, 0.54 ml of hydrazine hydrate and 50 ml water was heated for 2 hours at 100° C. After cooling the precipitated solid was filtered off, washed with water and dried.
Yield: 1.4 g. Melting point: 133°–135° C.
IR (in KBr): 1665, 1605 cm$^{-1}$
MS [m/e]: 274 (M$^+$, 13%), 193 (100%), 151 (21%), 135 (10%), 122 (45%).

EXAMPLE 2

6-[5-(1-Imidazolylmethyl)-thien-2-yl]-2-methyl-3-oxo-2,3,4,5-tetrahydro-pyridazine A mixture of 8.7 g of 4-[5-(1-imidazolylmethyl)-thien-2-yl]-4-oxobutyric acid, 2.9 ml methylhydrazine and 100 ml water was heated at 90° C. for 2 hours. After cooling, the precipitated solid was filtered off, dissolved in chloroform, the chloroform phase washed with dilute caustic soda solution and with water, dried over sodium sulfate and evaporated. The residue was purified by column chromatography (Silica gel//chloroform) and finally recrystallized from ethanol.
Yield: 1.6 g. Melting point: 121° C.
IR (in KBr): 1637 cm$^{-1}$
MS [m/e]: 274 (M$^+$, 39%), 207 (100%), 165 (6%), 149 (13%), 137 (6%), 122 (13%).

EXAMPLE 3

6-[5-(1-Imidazolylmethyl)-thien-2-yl]-3-oxo-2-phenyl-2,3,4,5-tetrahydro-pyridazine A mixture of 2.64 g of 4-[5-(1-imidazolylmethyl)-thien-2-yl]-4-oxobutyric acid, 1.12 g phenylhydrazine, 40 ml water and 40 ml ethanol was stirred for 10 hours under reflux. After cooling the mixture was evaporated, the residue shaken with chloroform/dilute caustic soda solution, the chloroform phase washed with water, dried and evaporated. The residue was recrystallized from diisopropyl ether/ethyl acetate.
Yield: 160 mg Melting point: 178° C.
IR (in KBr): 1628 cm$^{-1}$
MS [m/e]: 336 (M$^+$, 46%), 269 (73%), 122 (17%), 105 (74%), 77 (100%).

EXAMPLE 4

6-[4-(1-Imidazolylmethyl)-thien-2-yl]-3-oxo-2,3,4,5-tetrahydro-pyridazine

A mixture of 5.6 g of 4-[4-(1-imidazolylmethyl)-thien-2-yl]-4-oxobutyric acid, 1.1 g hydrazine hydrate and 50 ml water was stirred for 2 hours at 90° C. After cooling, the precipitated solid was filtered off, washed with water and dried.
Yield: 5.2 g Melting point: 178°–179° C.
IR (in KBr): 1670 cm$^{-1}$ MS [m/e]: 260 (M+, 47%), 193 (100%), 131 (5%), 122 (9%).

Similarly to Examples 1–4 there may be prepared:
6-{5-[2-(2-Methyl-1-imidazolyl)-ethyl]-thien-2-yl}-3-oxo-2,3,4,5-tetrahydro-pyridazine,
6-{5-[3-(2-Methyl-2-imidazolyl)-propyl]-thien-2-yl}-3-oxo-2,3,4,5-tetrahydro-pyridazine,
6-{5-[4-(2-Methyl-1-imidazolyl)-butyl]-thien-2-yl}-3-oxo-2,3,4,5-tetrahydro-pyridazine,
6-{5-[5-(2-Methyl-1-imidazolyl)-pentyl]-thien-2-yl}-3-oxo-2,3,4,5-tetrahydro-pyridazine,
6-{5-[6-(2-Methyl-1-imidazolyl)-hexyl]-thien-2-yl}-3-oxo-2,3,4,5-tetrahydro-pyridazine,
6-{5-[7-(2-Methyl-1-imidazolyl)-heptyl]-thien-2-yl}-3-oxo-2,3,4,5-tetrahydro-pyridazine,
6-{5-[8-(2-Methyl-1-imidazolyl)-octyl]-thien-2-yl}-3-oxo-2,3,4,5-tetrahydro-pyridazine,
6-[5-(2-Ethyl-1-imidazolylmethyl)-thien-2-yl]-3-oxo-2,3,4,5-tetrahydro-pyridazine,
6-[5-(2-propyl-1-imidazolylmethyl)-thien-2-yl]-3-oxo-2,3,4,5-tetrahydro-pyridazine,
6-[5-(1-Imidazolylmethyl)-thien-2-yl]-2-ethyl-3-oxo-2,3,4,5-tetrahydro-pyridazine,
6-[5-(1-Imidazolylmethyl)-thien-2-yl]-3-oxo-2-propyl-2,3,4,5-tetrahydro-pyridazine.

EXAMPLE 5

6-[5-(1-Imidazolyl)-thien-2-yl]-5-methyl-3-oxo-2,3,4,5-tetrahydro-pyridazine (a)
4-[5-(1-Imidazolyl)-thien-2-yl]-3-methyl-4-oxobutyronitrile A mixture of 14.7 g of 5-(1-imidazolyl)-thiophen-2-aldehyde (prepared as described by J. B. Polya et al, Chem.Soc.C. (1970), 85 ff, mp 105°–107° C.), 5.5 g 2-butenoic acid nitrile, 0.81 g of sodium cyanide and 200 ml of dimethylformamide was stirred for 16 hours at 25° C. under a nitrogen atmosphere. After addition of water the mixture was extracted with chloroform, the chloroform phase washed with water, dried, evaporated and the residue purified by column chromatography (Silica gel//chloroform/methanol).

Yield: 9.4 g Melting point: 112°–114° C.
IR (in KBr): 2245, 1648 cm$^{-1}$
MS [m/e]: 245 (M+, 37%), 177 (100%), 149 (17%), 122 (8%), 105 (14%).

(b)
4-[5-(1-Imidazolyl)-thien-2-yl]-3-methyl-4-oxobutyric acid 6.7 g of oxobutyronitrile was heated in 50 ml of 18% hydrochloric acid for 3 hours under reflux. After cooling, the pH was adjusted to 9 with caustic soda solution, and the mixture washed with chloroform. Then the pH was adjusted to 6.5. The precipitated solid was filtered off and dried. The filtrate was evaporated to a residual volume of 80 ml and forwarded to the next stage without further purification.

Yield: 0.45 g Melting point: 180°–182° C.
IR (in KBr): 1721, 1638 cm$^{-1}$
MS [m/e]: 264 (M+, 30%), 177 (100%), 149 (17%), 122 (8%), 105 (16%).

(c)
6-[5-(1-Imidazolyl)-thien-2-yl]-5-methyl-3-oxo-2,3,4,5-tetrahydro-pyridazine The aqueous solution (5b) is stirred with 3 ml of hydrazine hydrate for 2 hours at 90° C. The solid which precipitates on cooling is recrystallized from a small amount of chloroform.

Yield: 3.3 g Melting point: 239°–241° C.
IR (in KBr): 1677 cm$^{-1}$
MS [m/e]: 260 (M+, 100%), 245 (12%), 203 (16%), 189 (14%), 175 (6%), 149 (6%).

EXAMPLE 6

6-[5-(1-Imidazolyl)-thien-2-yl]-2,5-dimethyl-3-oxo-2,3,4,5-tetrahydro-pyridazine A mixture of 400 mg oxobutyric acid from Example (5b), 86 ml of methylhydrazine and 10 ml water was stirred for 2 hours at 90° C. After cooling the mixture was extracted with chloroform, the chloroform phase evaporated and the residue purified by thin layer chromatography (Silica gel-prepared plate 60 F 254, chloroform/methanol 90/10).

Yield: 14 mg Melting point: 134°–136° C.
Rf value: 0.53
MS [m/e]: 274 (M+, 100%), 259 (4%), 203 (16%), 189 (20%), 163 (6%), 71 (21%).

EXAMPLE 7

6-[5-(2-Methyl-1-imidazolyl)-thien-2-yl]-5-methyl-3-oxo-2,3,4,5-tetrahydro-pyridazine A mixture of 1 g of 5-(2-methyl-1-imidazolyl)-thiophen-2-aldehyde (mp 86°–88° C.), 700 mg of 2-butenoic acid nitrile, 41 mg of sodium cyanide and 25 ml dimethylformamide was stirred for 3 days under a nitrogen atmosphere. After addition of water the mixture was extracted with chloroform, the organic phase washed with water, dried and evaporated. The residue (300 mg) was kept at reflux temperature with 20 ml 18% hydrochloric acid for 2 hours. After cooling the mixture its pH was adjusted to 9 with caustic soda solution, the mixture extracted with chloroform and the aqueous phase adjusted to pH 7 with dilute hydrochloric acid. After evaporation to a residual volume of 50 ml, 0.5 ml of hydrazine hydrate was added and the mixture stirred for 18 hours at 90° C. After cooling and chloroform extraction, the extract was evaporated and the residue chromatographically purified (Silica gel prepared plate 60 F 254, chloroform/methanol 90/10).

Yield: 30 mg Melting point: 195°–197° C.
Rf value: 0.5
MS [m/e]: 274 (M+, 100%), 259 (9%), 217 (10%), 206 (16%).

EXAMPLE 8

6-[4-(1-Imidazolyl)-thien-2-yl]-5-methyl-3-oxo-2,3,4,5-tetrahydro-pyridazine (a)
4-[4-(1-Imidazolyl)-thien-2-yl]-3-methyl-4-oxobutyronitrile Similarly to Example (5a) the reaction is carried out with 6 g of 4-(1-imidazolyl)-thiophen-2-aldehyde (mp 127°–130° C.), 2.3 g of 2-butenoic acid nitrile, 0.45 g sodium cyanide and 50 ml dimethylformamide.

Yield: 3.9 g Melting point: 113° C.
IR (in KBr): 2252, 1654 cm$^{-1}$
MS [m/e]: 245 (M+, 38%), 177 (100%), 149 (11%), 122 (5%), 105 (12%).

(b)
4-[4-(1-Imidazolyl)-thien-2-yl]-3-methyl-4-oxobutyric acid 67 g of oxobutyronitrile from Example (8a) were heated under reflux for 5 hours in 600 ml of 16% hydrochloric acid. After cooling, the pH was adjusted to 6.4 with 6N caustic soda solution, the precipitated solid material was filtered off, washed with water and dried.

Yield: 63.3 g Melting point: 230°–231° C.
IR (in KBr): 1718, 1668 cm$^{-1}$
MS [m/e]: 264 (M$^+$, 39%), 195 (12%), 177 (100%), 149 (13%), 122 (5%), 105 (11%).

(c)
6-[4-(1-Imidazolyl)-thien-2-yl]-5-methyl-3-Oxo-2,3,4,5-tetrahydro-pyridazine 26.4 g oxobutyric acid from Example (8b) were stirred under reflux for 2 hours with 6 g of hydrazine hydrate in 200 ml water. The product which precipitated hot was filtered off hot, washed with water and dried.

Yield: 17.7 g Melting point: 225° C.
IR (in KBr): 1671 cm$^{-1}$
MS [m/e]: 260 (M$^+$, 100%), 245 (10%), 217 (3%), 203 (19%), 189 (16%), 176 (7%), 148 (7%), 121 (5%).

The following were prepared analogously to Examples 5–8:

6-[5-(1-Imidazolyl)-thien-2-yl]-3-oxo-2,3,4,5-tetrahydro-pyridazine,
6-[5-(1-Imidazolyl)-thien-2-yl]-2-methyl-3-oxo-2,3,4,5-tetrahydro-pyridazine,
6-[5-(1-Imidazolyl)-thien-2-yl]-4-methyl-3-oxo-2,3,4,5-tetrahydro-pyridazine,
6-[5-(1-Imidazolyl)-thien-2-yl]-5-ethyl-3-oxo-2,3,4,5-tetrahydro-pyridazine,
6-[5-(2-Methyl-1-imidazolyl)-thien-2-yl]-3-oxo-2,3,4,5-tetrahydro-pyridazine,
6-[5-(2-Ethyl-1-imidazolyl)-thien-2-yl]-5-methyl-3-oxo-2,3,4,5-tetrahydro-pyridazine,
6-[5-(2-Phenyl-1-imidazolyl)-thien-2-yl]-5-methyl-3-oxo-2,3,4,5-tetrahydro-pyridazine,
6-[4-(1-Imidazolyl)-thien-2-yl]-3-oxo-2,3,4,5-tetrahydro-pyridazine,
6-[4-(1-Imidazolyl)-thien-2-yl]-5-ethyl-3-oxo-2,3,4,5-tetrahydro-pyridazine,
6-[4-(2-Methyl-1-imidazolyl)-thien-2-yl]-5-methyl-3-oxo-2,3,4,5-tetrahydro-pyridazine.

EXAMPLE 9
6-[5-(1-Imidazolyl)-thien-2-yl]-5-methyl-3-oxo-2,3,4,5-tetrahydro-pyridazine fumarate A mixture of 200 mg of 6-[5-(1-imidazolyl)-thien-2-yl]-5-methyl-3-oxo-2,3,4,5-tetrahydro-pyridazine and 89 mg of fumaric acid was heated in 50 ml ethanol until solution was effected. Then the solution was evaporated and the residue dried.

Yield: 214 mg Melting point: 188°–190° C. (decomp)
IR (in KBr): 1708, 1650, 1615 cm$^{-1}$ Oxalates, succinates, malonates, citrates, tartrates etc as well as inorganic salts, such as hydrochlorides, hydrogen sulfates etc may for example be prepared analogously to Example 9.

What we claim is:
1. Imidazolylthien-2-yl-tetrahydropyridazines of the formula I

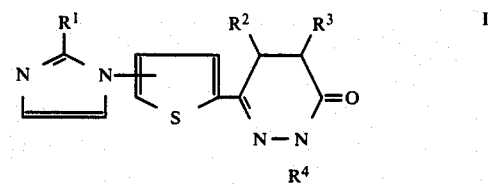

wherein $R^1$, $R^2$, $R^3$ and $R^4$ can be same or different and independently of each other denote hydrogen, $C_{1-4}$ lower alkyl, or phenyl and its pharmaceutically acceptable salts.

2. 6-[5-(1-Imidazolyl)-thien-2-yl]-5-methyl-3-oxo-2,3,4,5-tetrahydro-pyridazine and its pharmaceutically acceptable acid addition salts.

3. 6-[5-(1-Imidazolyl)-thien-2-yl]-2,5-dimethyl-3-oxo-2,3,4,5-tetrahydro-pyridazine and its pharmaceutically acceptable acid addition salts.

4. 6-[5-(2-Methyl-1-imidazolyl)-thien-2-yl]-5-methyl-3-oxo-2,3,4,5-tetrahydro-pyridazine and its pharmaceutically acceptable acid addition salts.

5. 6-[4-(1-Imidazolyl)-thien-2-yl]-5-methyl-3-oxo-2,3,4,5-tetrahydro-pyridazine and its pharmaceutically acceptable acid addition salts.

6. A process for the treatment of cardiovascular and/or thromboembolic illnesses in humans wherein a compound according to claim 1 is administered to a human being suffering from such an illness in an amount of 1.0 to 500 mg per dose between one and several times a day.

7. Process according to claim 6 wherein the compound of claim 1 is combined with a diuretic and/or a beta-blocker in usual dosages.

* * * * *